US008805527B2

(12) United States Patent
Mumford et al.

(10) Patent No.: US 8,805,527 B2
(45) Date of Patent: Aug. 12, 2014

(54) WIRELESS PHYSIOLOGICAL MONITORING

(75) Inventors: John Robert Mumford, Mississauga (CA); Ronald Leon Kurtz, Oakville (CA)

(73) Assignee: Natus Medical Incorporated, San Carlos, CA (US)

( * ) Notice: Subject to any disclaimer, the term of this patent is extended or adjusted under 35 U.S.C. 154(b) by 1589 days.

(21) Appl. No.: 12/332,105

(22) Filed: Dec. 10, 2008

(65) Prior Publication Data

US 2009/0088608 A1   Apr. 2, 2009

Related U.S. Application Data

(63) Continuation of application No. 11/130,221, filed on May 17, 2005, now abandoned.

(60) Provisional application No. 60/571,890, filed on May 18, 2004, provisional application No. 60/571,944, filed on May 18, 2004, provisional application No. 60/571,942, filed on May 18, 2004.

(51) Int. Cl.
| | |
|---|---|
| *A61N 1/00* | (2006.01) |
| *A61B 5/00* | (2006.01) |
| *A61N 1/36* | (2006.01) |
| *A61N 1/04* | (2006.01) |
| *A61N 1/05* | (2006.01) |

(52) U.S. Cl.
CPC .......... *A61N 1/36017* (2013.01); *A61B 5/0002* (2013.01); *A61N 1/0502* (2013.01); *A61N 1/36014* (2013.01); *A61N 1/0456* (2013.01)
USPC .......................................... 607/60

(58) Field of Classification Search
CPC ............ A61N 1/3727; A61N 1/37211; A61N 1/37217; A61N 1/37282; A61N 1/37288; A61N 1/37252
USPC ................ 607/60, 32; 600/509; 128/903, 904
See application file for complete search history.

(56) References Cited

U.S. PATENT DOCUMENTS

| | | | | |
|---|---|---|---|---|
| 4,886,064 | A | * | 12/1989 | Strandberg ..................... 607/18 |
| 5,081,543 | A | | 1/1992 | Romandi |
| 5,168,874 | A | * | 12/1992 | Segalowitz .................. 600/393 |
| 5,222,503 | A | | 6/1993 | Ives et al. |
| 5,233,999 | A | | 8/1993 | Dellacorna et al. |

(Continued)

FOREIGN PATENT DOCUMENTS

WO    WO90/08501 A1    8/1990

*Primary Examiner* — Christopher D Koharski
*Assistant Examiner* — Roland Dinga
(74) *Attorney, Agent, or Firm* — Temmerman Law Office; Mathew J. Temmerman

(57) ABSTRACT

Embodiments of the invention relate to a wireless physiological monitoring system. The system includes at least one wireless sensor and a monitoring device which are linked to one another of a wireless fashion for measuring physiological signals of a patient. The at least one wireless sensor is located on the patient and may comprise a wireless surface electrode assembly or a wireless needle assembly. The system may also comprise a wireless stimulator synchronized with the wireless sensor for performing certain diagnostic tests, such as nerve conduction velocity tests, for example. The wireless sensor preferably includes active, reference and common conductors. The common conductor can be used to measure the common mode voltage of the patient in the vicinity of the testing, and this voltage can then be subtracted from the measured active and reference voltages.

4 Claims, 3 Drawing Sheets

(56) References Cited

U.S. PATENT DOCUMENTS

| | | | |
|---|---|---|---|
| 5,307,818 A | 5/1994 | Segalowitz | |
| 5,394,882 A * | 3/1995 | Mawhinney | 600/534 |
| 5,411,535 A * | 5/1995 | Fujii et al. | 607/32 |
| 5,417,222 A * | 5/1995 | Dempsey et al. | 600/509 |
| 5,458,124 A | 10/1995 | Stanko et al. | |
| 5,511,553 A * | 4/1996 | Segalowitz | 600/508 |
| 5,544,661 A * | 8/1996 | Davis et al. | 600/513 |
| 5,579,781 A | 12/1996 | Cooke | |
| 5,747,983 A | 5/1998 | Lara et al. | |
| 5,755,230 A * | 5/1998 | Schmidt et al. | 600/544 |
| 5,838,223 A | 11/1998 | Gallant et al. | |
| 5,862,803 A * | 1/1999 | Besson et al. | 600/508 |
| 5,871,451 A | 2/1999 | Unger et al. | |
| 5,904,708 A * | 5/1999 | Goedeke | 607/18 |
| 5,924,074 A | 7/1999 | Evans | |
| 5,944,659 A | 8/1999 | Flach et al. | |
| 5,957,854 A | 9/1999 | Besson et al. | |
| 5,957,860 A | 9/1999 | Rodiera | |
| 5,959,287 A | 9/1999 | Myers et al. | |
| 5,964,701 A | 10/1999 | Asada et al. | |
| 5,971,931 A | 10/1999 | Raff | |
| 5,987,335 A | 11/1999 | Knoedl et al. | |
| 6,026,321 A | 2/2000 | Miyata et al. | |
| 6,093,146 A | 7/2000 | Filangeri | |
| 6,161,036 A * | 12/2000 | Matsumura et al. | 600/509 |
| 6,213,942 B1 | 4/2001 | Flach et al. | |
| 6,230,049 B1 | 5/2001 | Fischell et al. | |
| 6,289,238 B1 | 9/2001 | Besson et al. | |
| 6,295,466 B1 * | 9/2001 | Ishikawa et al. | 600/509 |
| 6,434,420 B1 | 8/2002 | Taheri | |
| 6,434,421 B1 | 8/2002 | Taheri | |
| 6,438,413 B1 | 8/2002 | Taheri | |
| 6,441,747 B1 * | 8/2002 | Khair et al. | 340/870.16 |
| 6,443,890 B1 | 9/2002 | Schulze et al. | |
| 6,445,299 B1 | 9/2002 | Rojas, Jr. | |
| 6,445,955 B1 * | 9/2002 | Michelson et al. | 607/46 |
| 6,470,893 B1 * | 10/2002 | Boesen | 128/899 |
| 6,493,568 B1 | 12/2002 | Bell et al. | |
| 6,496,705 B1 * | 12/2002 | Ng et al. | 455/502 |
| 6,544,173 B2 | 4/2003 | West et al. | |
| 6,577,893 B1 * | 6/2003 | Besson et al. | 600/509 |
| 6,577,901 B2 | 6/2003 | Thompson | |
| 6,589,170 B1 | 7/2003 | Flach et al. | |
| 6,611,705 B2 | 8/2003 | Hopman et al. | |
| 6,616,606 B1 | 9/2003 | Petersen et al. | |
| 6,643,541 B2 * | 11/2003 | Mok et al. | 600/546 |
| 6,654,631 B1 | 11/2003 | Sahai | |
| 6,662,052 B1 * | 12/2003 | Sarwal et al. | 607/59 |
| 6,675,219 B1 | 1/2004 | Leppinen et al. | |
| 6,686,910 B2 | 2/2004 | O'Donnell, Jr. | |
| 6,690,959 B2 | 2/2004 | Thompson | |
| 6,712,754 B2 | 3/2004 | Miller et al. | |
| 6,987,965 B2 * | 1/2006 | Ng et al. | 455/419 |
| 2001/0023315 A1 | 9/2001 | Flach et al. | |
| 2001/0034475 A1 | 10/2001 | Flach et al. | |
| 2002/0013518 A1 | 1/2002 | West et al. | |
| 2002/0035484 A1 | 3/2002 | McCormick | |
| 2002/0036619 A1 | 3/2002 | Simmon et al. | |
| 2002/0072682 A1 | 6/2002 | Hopman et al. | |
| 2002/0111542 A1 * | 8/2002 | Warkentin et al. | 600/300 |
| 2002/0115914 A1 * | 8/2002 | Russ | 600/300 |
| 2002/0123672 A1 * | 9/2002 | Christophersom et al. | 600/300 |
| 2002/0123673 A1 * | 9/2002 | Webb et al. | 600/300 |
| 2002/0126036 A1 | 9/2002 | Flaherty et al. | |
| 2002/0145526 A1 | 10/2002 | Friedman et al. | |
| 2002/0152107 A1 | 10/2002 | Mifune et al. | |
| 2002/0198604 A1 * | 12/2002 | Schulman et al. | 623/25 |
| 2003/0035084 A1 | 2/2003 | Mmakino | |
| 2003/0040305 A1 | 2/2003 | Ng et al. | |
| 2003/0045787 A1 | 3/2003 | Schulze et al. | |
| 2003/0109905 A1 | 6/2003 | Mok et al. | |
| 2003/0163350 A1 | 8/2003 | Rudowski et al. | |
| 2003/0186672 A1 | 10/2003 | Buchaillot et al. | |
| 2003/0199777 A1 | 10/2003 | Hopman et al. | |
| 2003/0229274 A1 | 12/2003 | Standeven | |
| 2004/0015058 A1 | 1/2004 | Besson et al. | |
| 2004/0019369 A1 * | 1/2004 | Duncan et al. | 607/46 |
| 2004/0026519 A1 | 2/2004 | Usami et al. | |
| 2004/0049240 A1 | 3/2004 | Gerber et al. | |
| 2004/0054263 A1 | 3/2004 | Moerman et al. | |
| 2004/0068195 A1 * | 4/2004 | Massicotte et al. | 600/509 |
| 2004/0068196 A1 | 4/2004 | Massicotte et al. | |
| 2004/0073127 A1 | 4/2004 | Istvan et al. | |
| 2004/0088027 A1 * | 5/2004 | Burnes et al. | 607/60 |
| 2004/0106858 A1 * | 6/2004 | Say et al. | 600/345 |
| 2004/0199056 A1 * | 10/2004 | Husemann et al. | 600/300 |
| 2005/0101843 A1 * | 5/2005 | Quinn et al. | 600/300 |

* cited by examiner

WIRELESS PHYSIOLOGICAL MONITORING

RELATED APPLICATIONS

This application is a continuation of U.S. patent application Ser. No. 11/130,221 filed on May 17, 2005 which claims the benefit of U.S. Provisional Patent Application Ser. No. 60/571,944 filed on May 18, 2004, the entire contents of which are hereby incorporated by reference, U.S. Provisional Patent Application Ser. No. 60/571,890, filed on May 18, 2004, the entire contents of which are hereby incorporated by reference and U.S. Provisional Patent Application Ser. No. 60/571,942 filed on May 18, 2004, the entire contents of which are hereby incorporated by reference.

FIELD OF THE INVENTION

The invention relates to a wireless physiological monitoring system that can be used to measure a wide variety of physiological signals from a patient for monitoring the patient and/or diagnosing certain medical conditions.

BACKGROUND OF THE INVENTION

The measurement of physiological signals from a patient for monitoring the patient and/or diagnosing a particular medical condition conventionally requires medical instrumentation to be physically attached to the patient. This includes attaching electrodes to the patient at the measurement site and then transmitting the measured signals to the medical instrumentation via cables. In some cases, this can result in many cables being connected between the patient and the medical instrumentation. For instance, for multimodality intraoperative monitoring measurements, there may be anywhere from 4 to 32 measurement channels, for electromyography (EMG) measurements there may be 1 to 4 measurement channels, for electrocardiogram (ECG) measurements, there may be ten measurement channels and for measuring brain potentials, there may be more than 128 channels in cases where signals are measured from the cortex.

The plurality of cables connecting the patient to the medical instrumentation provides many disadvantages. The cables are uncomfortable for the patient and limit the mobility of the patient. It is important for the patient to remain mobile so that the patient does not develop any blood clots. The cables also make it difficult to perform any tests on the patient which require the patient to move. Further, in some cases, the cables may be stiff and can easily become detached from the patient especially when the patient moves.

The plurality of cables connecting the patient to the medical instrumentation are also cumbersome for the medical personnel that interact with the patient. In particular, the entire set-up can be confusing and in some cases requires expertise for arranging all of the different electrodes and cables. Accordingly, the time required for attaching or removing the electrodes and cables to or from the patient can be quite long. This can be detrimental in situations in which speed is of the essence. In addition, the medical personnel may accidentally trip or become entangled in the cables. Further, in the operating room, the cables to the patient are not accessible during surgery since the cables are in the "sterile field". This is a problem when troubleshooting faulty cables since cables in the operating room are routinely run over by people and heavy equipment and therefore subject to a high failure rate.

SUMMARY OF THE INVENTION

The inventors have developed a wireless physiological monitoring system that includes, at a minimum, at least one wireless sensor and a monitoring device which are linked to one another in a wireless fashion for measuring physiological signals from a patient for monitoring the patient. The wireless physiological monitoring system may also be used to perform diagnostic tests on the patient. To perform certain diagnostic tests, the wireless physiological monitoring system may further include a wireless stimulator that is synchronized with the wireless sensor for performing certain diagnostic tests such as nerve conduction velocity tests, for example.

In one instance, the wireless sensor may be a wireless surface electrode assembly. In another instance, the wireless sensor may be a wireless needle assembly. In both cases, the sensors preferably include electrical leads for obtaining active, reference and common voltage measurements. This results in better signal quality for the measured physiological signals since the common mode voltage can be measured and removed from both the measured active and reference voltages. The wireless needle assembly is also advantageous in that it requires no external surface electrodes to operate.

For both the wireless surface electrode assembly and the wireless needle assembly, the sensors include a releasably attachable wireless adapter that provides a wireless connection between the sensor and the monitoring device, and a measurement module, for measuring physiological signals from the patient. The measurement module is disposable and the wireless adapter may be reused with another measurement module to form another wireless sensor.

In one instance, the wireless adapter may communicate according to the Bluetooth communication protocol.

Further, in one embodiment, the wireless adapter includes a processor and a pre-processing stage for processing the measured physiological signals prior to transmitting corresponding wireless signals to the monitoring device. The wireless adapter may also include a memory unit for storing the raw measured or processed physiological signals.

The wireless physiological monitoring system of the invention advantageously allows for faster application and removal of the sensors to a patient since there are no cables that need to be attached. When the wireless needle assembly is used as the wireless sensor, the medical practitioner simply places the needle assembly into the recording site and receives high quality signals through the wireless connection without the need to prepare and "wire-up" the patient. The wireless physiological monitoring system provides better signal quality for the measured physiological signals since there are no cables which can pick up electromagnetic interference; this is a common problem with conventional equipment. There is also no leakage current once the measured physiological signals have been converted to wireless signals. Furthermore, since all of the components of the wireless physiological monitoring system are totally wireless, the mobility of the patient is not compromised.

In a first aspect, the invention provides a wireless physiological monitoring system for measuring physiological signals from a patient. The system comprises a monitoring device having a first transceiver; at least one wireless sensor disposed on a measurement site on the patient for measuring a physiological signal, the at least one wireless sensor having a second transceiver for transmitting a corresponding wireless physiological signal to the first transceiver; and, at least one wireless stimulator having a third transceiver, the at least one wireless stimulator being adapted to provide a stimulation current to the patient in response to at least one of a command signal transmitted by the first transceiver of the monitoring device and manual actuation.

In one embodiment, the at least one wireless sensor includes a wireless adapter having the second transceiver;

and, a measurement module having an active conductor and a reference conductor for receiving voltages used to produce a differential voltage measurement indicative of the physiological signal, the measurement module further including a common conductor for receiving another voltage for removing common mode voltage from the differential measurement. The second transceiver transmits the differential measurement as the wireless physiological signal.

In another embodiment, a wireless surface electrode assembly is used for the at least one wireless sensor. The measurement module of the wireless electrode assembly comprises: a base having an electrical interface connected to the active, reference and common conductors, the base having a shape complementary to that of the wireless adapter for releasable attachment to the wireless adapter; an active electrode for placement on the patient, the active electrode being connected to the active conductor; a reference electrode for placement on the patient, the reference electrode being connected to the reference conductor; and, a common electrode for placement on the patient, the common electrode being connected to the common conductor.

The active and reference electrodes are located approximately equidistantly from the common electrode.

In another embodiment, a wireless needle assembly is used for the at least one wireless sensor. The measurement module of the wireless needle assembly comprises: a base having an electrical interface connected to the active, reference and common conductors, the base having a shape complementary to that of the wireless adapter for releasable attachment to the wireless adapter; and, a shaft which houses the active, reference and common conductors, wherein a first conductor is disposed centrally along the longitudinal axis of the shaft, a second conductor is disposed concentrically about the first conductor, a first insulator is disposed in between the first and second conductors, a third conductor is disposed concentrically about the second conductor, and a second insulator is disposed in between the second and third conductors.

In a second aspect, the invention provides a wireless physiological monitoring system for measuring physiological signals from a patient. The system comprises a monitoring device having a first transceiver; and, at least one wireless sensor disposed on a measurement site on the patient for measuring a physiological signal. The at least one wireless sensor includes a wireless adapter having a second transceiver; and, a measurement module having an active conductor and a reference conductor for receiving voltages used to produce a differential voltage measurement indicative of the physiological signal, the measurement module further including a common conductor for receiving another voltage for removing common mode voltage from the differential measurement. The second transceiver transmits a wireless physiological signal corresponding to the differential voltage measurement to the first transceiver of the monitoring device.

In one embodiment, the system further comprises at least one wireless stimulator having a third transceiver, the at least one wireless stimulator being adapted to provide a stimulation current to the patient in response to at least one of a command signal transmitted by the first transceiver of the monitoring device and manual actuation.

In a third aspect, the invention provides a wireless sensor for measuring a physiological signal from a patient, the wireless sensor being disposed on a measurement site on the patient. The wireless sensor comprises: a wireless adapter having a transceiver; and, a measurement module having an active conductor and a reference conductor for receiving voltages used to produce a differential voltage measurement indicative of the physiological signal, the measurement module further including a common conductor for receiving another voltage for removing common mode voltage from the differential measurement. The transceiver transmits a wireless physiological signal corresponding to the differential voltage measurement.

BRIEF DESCRIPTION OF THE DRAWINGS

For a better understanding of the invention and to show more clearly how it may be carried into effect, reference will now be made, by way of example only, to the accompanying drawings which show exemplary embodiments of the invention and in which.

DETAILED DESCRIPTION OF THE EMBODIMENTS OF THE INVENTION

Figure 1:
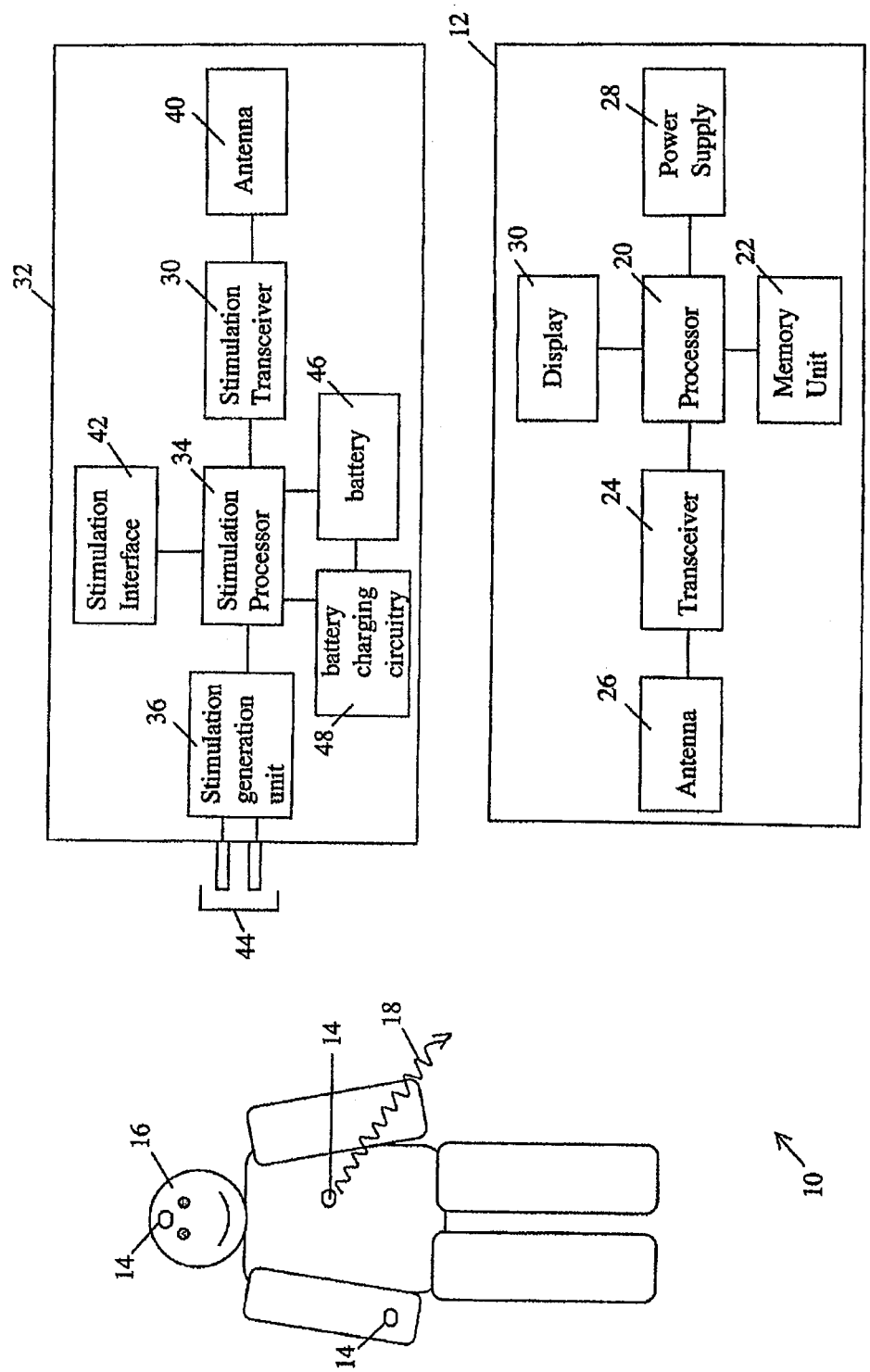
FIG. 1 shows an exemplary embodiment of a wireless physiological monitoring system in accordance with the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements. In addition, numerous specific details are set forth in order to provide a thorough understanding of the invention. However, it will be understood by those of ordinary skill in the art that the invention may be practiced without these specific details. In other instances, well-known methods, procedures and components have not been described in detail so as not to obscure the invention.

Referring first to FIG. 1, shown therein is an exemplary embodiment of a wireless physiological monitoring system 10. The wireless physiological monitoring system 10 comprises a monitoring device 12 and at least one wireless sensor 14. Typically there are a plurality of wireless sensors 14, three of which are shown for exemplary purposes. The wireless sensors 14 are attached to a patient 16 and each measures a desired physiological signal from the patient 16. Examples of physiological signals include an electroencephalographic (EEG) signal, an electrooculographic (EOG) signal, an electromyographic (EMG) signal or an electrocardiographic (ECG) signal. The measured physiological signal may be pre-processed by the wireless sensor 14. The wireless sensors 14 then transmit corresponding wireless physiological signals 18 to the monitoring device 12. The transmission frequency may be in the Wireless Medical Telemetry Services (WMTS) band or the Industry Scientific and Medical (ISM) band or any other band approved for this activity. The WMTS band includes frequency ranges of 608 to 614 MHz, 1395 to 1400 MHz and 1429 to 1432 MHz. The ISM band includes the frequency range of 2.4 to 2.4835 GHz. The structure of the wireless sensor 14 is discussed in more detail below.

The monitoring device 12 may perform a number of functions on the wireless physiological signals 18. For instance, the monitoring device 12 may simply store the wireless physiological signals 18 for later downloading to a computing device which processes the wireless physiological signals 18. In this case, the monitoring device 12 may simply be a storage device. Alternatively, the monitoring device 12 may itself process the wireless physiological signals 18 as well as possibly display the wireless physiological signals 18 of the processed version. Accordingly, the monitoring device 12 may be a suitable computing device such as a laptop computer, a personal computer (PC) or an application specific hardware device.

In one exemplary embodiment, the monitoring device 12 comprises a processor 20, a memory unit 22, a transceiver 24 with an antenna 26, a power supply 28 and a display 30 connected as shown in FIG. 1. The processor 20 controls the operation of the monitoring device 12 and initiates monitoring and/or diagnostic tests on the patient 16 via the wireless sensors 14. In particular, the processor 20 sends commands via the transceiver 24 to the wireless sensors 14 to initiate monitoring or diagnostic tests and also to synchronize with the wireless sensors 14. The processor 20 may be any suitable processing element, such as a PC central processing unit (CPU) chip, and in some instances may be a digital signal processor (DSP). The transceiver 24 operates according to a suitable wireless communication protocol. In one instance, the communication protocol may be the Bluetooth communication protocol as discussed in more detail below.

The processor 20 receives the wireless physiological signals 18 and stores the wireless physiological signals 18 in the memory unit 22. The memory unit 22 may be any suitable memory device such as a hard drive or flash memory or the like. The wireless physiological signals 18 can then be downloaded, via the transceiver 24, or another suitable communications device (not shown), to another computing device for processing. Alternatively, prior to storage or after storage, the processor 20 may then process the wireless physiological signals 18 according to a processing algorithm that is suitable for the type of monitoring or diagnostic test that is being performed. For instance, noise reduction algorithms may be applied to the signals 18 to improve the signal to noise ratio. In addition, pattern recognition or other detection algorithms may be applied to the signals 18 to detect certain events in the signals 18. These noise reduction and pattern recognition algorithms are commonly known to those skilled in the art and will not be discussed further.

The processor 20 may display the wireless physiological signals 18 or the processed version of the signals 18 on the display unit 30. The display 30 may be a monitor, an LCD, and the like. The power supply 28 provides power to the various components of the monitoring device 12. The power supply 28 may be a rechargeable battery or may be a computer power supply unit that is connected to mains power.

The wireless physiological monitoring system 10 may further comprise at least one wireless stimulator 32 for performing certain diagnostic tests on the patient 16 such as nerve conduction velocity tests. In particular, the wireless stimulator 32 is used to generate a stimulation current to create an action potential in a nerve of the patient 16.

The wireless stimulator 32 includes a stimulation processor 34, a stimulation generation unit 36, a stimulation transceiver 38 with an antenna 40, a stimulation interface 42, two prongs 44 and a battery 46 connected as shown in FIG. 1. The wireless stimulator 32 may optionally include battery charging circuitry 48. The stimulation processor 34 controls the operation of the wireless stimulator 32 and may be a DSP or a microcontroller. The stimulation processor 34 instructs the stimulation generation unit 36 to generate a stimulation current when the stimulation transceiver 38 receives an appropriate command signal from the monitoring device 12 or when it is manually actuated.

The stimulation generation unit 36 includes circuitry to create the stimulation current having different characteristics depending on the part of the patient 16 to which the stimulation current is being applied. In general, the stimulation current is preferably a controlled constant amplitude current and may include a single pulse or multiple pulses where each pulse may be monophasic or biphasic. For example, when the stimulation current is applied to the hand of the patient 16, the amplitude may be up to 100 milliamps, the duration of up to 1 millisecond and the maximum voltage is limited to 400 volts. However, when the wireless stimulator 32 is applied to the head of the patient 16, it is used to generate motor-evoked potentials and requires higher amplitude voltages and current. In such an instance, the maximum voltage amplitude is limited to 1000 V, the maximum current amplitude is limited to 1.5 A and the maximum pulse duration is less than 1 ms.

The stimulation interface 42 allows a medical practitioner to control the wireless stimulator 32. In one embodiment, the stimulation interface 42 includes a button, a dial and a small display (all not shown). The button may be manually actuated to start and stop the stimulation current, and the dial may be used to change the intensity of the stimulation current. The display shows the intensity of the stimulation current and the remaining charge on the battery. Alternatively, as previously mentioned, the wireless stimulator 32 may be controlled from the monitoring device 12 over the wireless link. In both cases, the same level of synchronization is needed between the wireless stimulator 32 and the corresponding wireless sensors 14 that are used to measure the response to the stimulation current.

During a diagnostic test, the two prongs 44 of the wireless stimulator 32 are applied to a test site on the skin of the patient 16 to stimulate the desired nerve. One of the prongs is a cathode terminal and the other prong is an anode terminal. The wireless stimulator 32 also has touch-proof adapter connections (not shown) to stimulate through smaller external electrodes or needles for cases in which the prongs 44 are not appropriate.

The wireless stimulator 32 is powered by the battery 46. In one embodiment, the battery 46 is a rechargeable battery. Accordingly, when the wireless stimulator 32 is not in use, the wireless stimulator 32 is placed in a charging stand (not shown) for recharging the battery 46. In this case, the stimulation processor 34 engages the battery charging circuitry 48 to recharge the battery 46.

There are some diagnostic tests in which it is beneficial to have two wireless stimulators. One example of such a diagnostic test is a collision study. One of the wireless stimulators is used to generate multiple action potentials resulting in a muscle or nerve response from the patient 16 and the other wireless stimulator is used to generate a second action potential in a different nerve that cancels out an undesirable response detected at the recording site. For this diagnostic test, the timing between the delivery of the stimulation currents provided by the two wireless stimulators must be controlled to an accuracy of a few hundred microseconds.

Figure 2A:
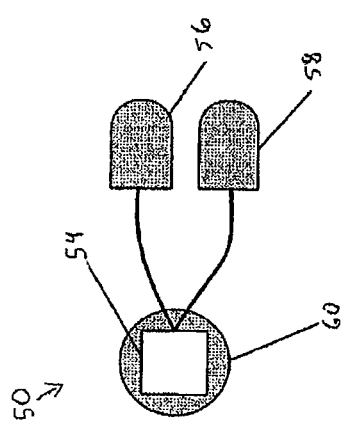
FIG. 2a shows a top view of an exemplary embodiment of a wireless surface electrode assembly for use as a wireless sensor in the system of FIG. 1 in accordance with the invention.
Figure 2B:
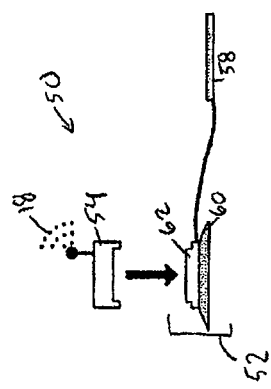
FIG. 2b shows an exploded side view of an exemplary embodiment of a wireless surface electrode assembly for use as a wireless sensor in the system of FIG. 1 in accordance with the invention.

Referring now to FIGS. 2a and 2b, shown therein is an exemplary wireless surface electrode assembly 50 for use as at least one of the wireless sensors 14 in the wireless physiological monitoring system 10. The wireless surface electrode assembly 50 includes a measurement module 52 and a wireless adapter 54. The measurement module 52 includes three conductive electrodes: an active electrode 56, a reference electrode 58 and a common electrode 60. The three electrodes 56, 58 and 60 are used so that a differential measurement is made for the desired physiological signal and so that the common mode of the differential measurement can be removed. The common electrode 60 is preferably equidistant to both the active and reference electrodes 56 and 58 so that the voltage measured by the common electrode 60 is common to both the active and reference electrodes 56 and 58. The signal provided by the common electrode 60 also allows for removing muscle artifacts from the physiological signals measured by the active and reference electrodes 56 and 58. The electrodes can be made of any biocompatible conductive material with suitable mechanical properties, such as silver-silver chloride, gold, silver, tin, platinum or alloys thereof, or carbon.

Each of the electrodes 56, 58 and 60 are wired to a base 62 of the measurement module 52 and are electrically insulated from one another. The base may be made of any biocompatible material with suitable mechanical properties, such as Nylon, Teflon or PVC. The base 62 further includes three electrical contacts (not shown) on a top portion thereof that interface with corresponding electrical contacts (not shown) on the bottom of the wireless adapter 54. The wireless adapter 54 includes components for transmitting the wireless physiological signal 18 that corresponds to the physiological signal measured by the electrode assembly 50 to the monitoring device 12. An exemplary implementation of the wireless adapter 54 is described below.

The wireless adapter 54 has a shape that is complementary to that of the measurement module 52 so that the wireless adapter 54 makes a snap-fit or friction-fit connection with the measurement module 52. The connection is also such that the wireless adapter 54 is releasably attachable to the measurement module 52. Accordingly, the wireless adapter 54 can be attached to a measurement module 52, used for physiological monitoring or diagnostic testing on the patient 16, and then detached from the measurement module 52 once monitoring/testing is completed so that the wireless adapter 54 can be reused and the measurement module 52 can be discarded.

The wireless surface electrode assembly 50 further includes an adhesive portion preferably applied to a section of each of the electrodes 56, 58 and 60 to hold the wireless surface electrode assembly 50 in place once the assembly 50 has been attached to the patient 16. Alternatively, or in addition, a piece of tape, or other adhesive means, may be applied to the electrodes 56, 58 and 60 of the wireless surface electrode assembly 50 to hold it in place. The electrodes may also be glued on with a suitable glue such as collodion. Alternatively, the wireless surface electrode assembly 50 may be built into gloves that are worn and held in place by a medical practitioner that is obtaining physiological signals from the patient 16.

Figure 3B:
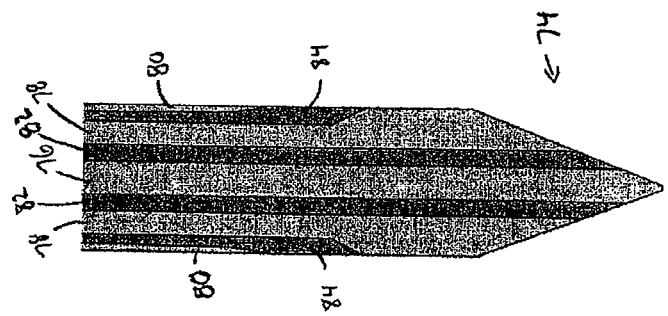
FIG. 3b shows a magnified view of an exemplary embodiment of the tip of the wireless needle assembly of FIG. 3a; and, FIG. 4 shows an exemplary embodiment of a wireless adapter for use with either the wireless surface electrode assembly of FIGS. 2a and 2b or the wireless needle assembly of FIGS. 3a and 3b.
Figure 3A:
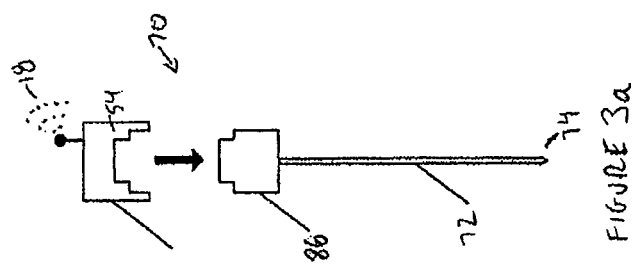
FIG. 3a shows an exploded side view of an exemplary embodiment of a wireless needle assembly for use as a wireless sensor in the system of FIG. 1 in accordance with the invention.

Referring now to FIGS. 3a and 3b, shown therein are an exploded side view, and a magnified view of the tip, respectively, of an exemplary embodiment of a wireless needle assembly 70, for use as at least one of the wireless sensors 14 in the wireless physiological monitoring system 10.

The wireless needle assembly 70 includes a measurement module 72 and the wireless adapter 54. The measurement module 72 includes a shaft with a needle tip 74 disposed at the end; the shaft and needle tip having three concentric conductors: an active conductor 76, a reference conductor 78 and a common conductor 80. The active and reference conductors 76 and 78 are separated by an insulator 82. The reference and common conductors 78 and 80 are separated by an insulator 84. The three conductors 76, 78 and 80 are used, in a similar manner to wireless sensor 50, so that a differential measurement may be made for the desired physiological signal and so that the common mode component of the differential measurement may be removed.

The common conductor 80 is advantageously in close proximity to both of the active conductor 76 and the reference conductor 78 so that it provides a close approximation to the common mode voltage of the active and reference conductors 76 and 78. It should be noted that the location of the reference, common and active conductors 76, 78 and 80 are interchangeable. For instance, the center conductor 76 may instead be the common conductor and the outer electrode 80 may be the active conductor. However, it is preferable for the active and reference conductors 76 and 78 to remain close to one another to eliminate any far field effects in the measured voltages. Accordingly, the common conductor 80 is preferably the outer conductor.

Each of the conductors 76, 78 and 80 are wired to a base 86 of the measurement module 72. The base 86 further includes three electrical contacts on a top portion thereof that interface with corresponding electrical contacts on the bottom of the wireless adapter 54. Similar to the wireless surface electrode assembly 50, the wireless adapter 54 has a shape that is complementary to that of the measurement module 72 so that the wireless adapter 54 is releasably attachable to the measurement module 72. Accordingly, the wireless adapter 52 is reusable and the measurement module 72 is disposable. The entire wireless needle assembly 70 is small enough to facilitate clinical use. Further, the tip 74 of the wireless needle assembly 70 may come in different lengths and diameters to facilitate measurement at muscles or nerves of different sizes and depths. Further details of the needle used by wireless needle assembly 70 are shown and described in co-pending U.S. patent application Ser. No. 11/130,222, filed May 17, 2005 and entitled "Needle Having Multiple Electrodes", the entire contents of which is hereby incorporated by reference.

In use, the wireless needle assembly 70 is inserted into a desired measurement site on the patient. To hold the wireless needle assembly 70 in place, a piece of tape, or other adhesive means, may be applied to the wireless needle assembly 70. The wireless needle assembly 70 may also be held in place by the hand of the medical practitioner who is measuring physiological signals from the patient 16. Alternatively, the wireless needle assembly 70 may not need any tape or adhesive if it is inserted to an adequate depth. In another alternative, the tip of the wireless needle assembly 70 may have a hook or corkscrew shape to hold it in place.

It should also be noted that the wireless adapter 54 may be used with other needles having a different number of conductors. For instance, the wireless adapter 54 may be combined with a measurement module that has a standard monopolar conductor configuration or with a measurement module that has a standard bipolar conductor configuration. In these cases, if a differential voltage measurement is to be made while removing common-mode voltage, extra surface electrodes can be attached to the measurement module. For instance, in the case of a needle measurement module having a standard monopolar (single active electrode) conductor configuration, a common surface electrode and a reference surface electrode may be added. In the case of a needle measurement module having a standard bipolar conductor configuration (having active and reference electrodes), only a common surface electrode need be added.

Figure 4:
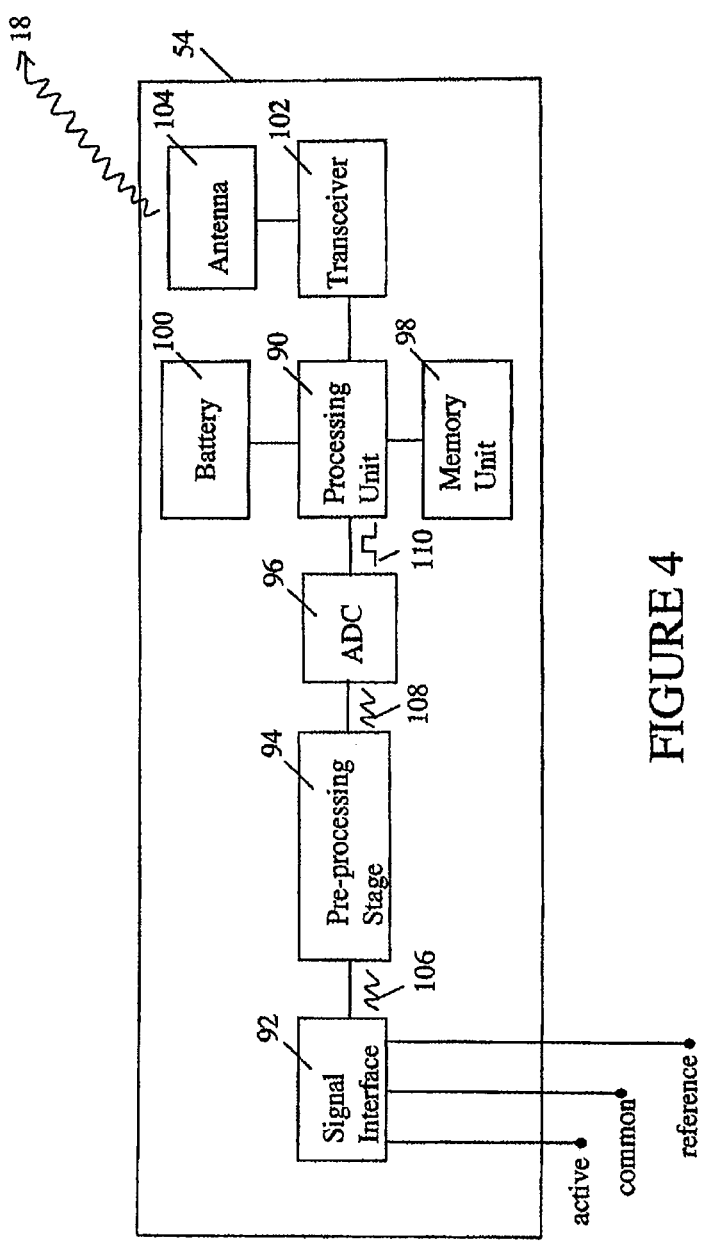

Referring now to FIG. 4, shown therein is an exemplary embodiment of the wireless adapter 54 for use with either the wireless surface electrode assembly 50 or the wireless needle assembly 70. The wireless adapter 54 includes a processing unit 90, a signal interface 92, a pre-processing stage 94, an analog-to-digital converter (ADC) 96, a memory unit 98, a battery 100, a transceiver 102 and an antenna 104 connected as shown in FIG. 4. The processing unit 90 controls the operation of the wireless adapter 54 and may be a DSP or the like.

The electrical interface 92 provides an electrical connection to the active, common and reference leads of the measurement modules 52 or 72 to receive measurement signals 106. The measurement signals 106 are then processed by the pre-processing stage 94 which includes a filtering stage followed by an amplification stage (both not shown). The filtering stage includes high pass filters (i.e. one for each of the active and reference measurement signals) to remove the contact potential component from the measurement signals 106 and provide filtered signals. It may also have a sine wave generator used for measuring impedance of the electrodes. The cutoff-frequency of the high pass filters is approximately 0.1 Hz to 20 Hz.

The amplification stage includes a differential amplifier for amplifying the filtered signals thereby providing pre-processed physiological signal 108. The gain factor of the amplifiers is selected so that the pre-processed physiological signal 108 does not saturate the input stage of the ADC 96. This depends on the type of physiological signals that are measured by the corresponding measurement module 52 or 72 (i.e. since different physiological signals have different amplitudes). The particular type of physiological signal that is being measured may be transmitted by the monitoring device 12 to the wireless adapter 54 so that the processing unit 90 can vary the gain of the amplification stage in the pre-processing stage 94.

The ADC 96 digitizes the pre-processed physiological signal 108 to provide a digitized physiological signal 110. The processing unit 90 sends the digitized physiological signal 110 to the transceiver 102 for transmitting the corresponding physiological wireless signal 18 via the antenna 104. The wireless physiological signal 18 may be transmitted at different rates depending on the type of physiological measurement that is made.

Prior to sending the digitized physiological signals 110 to the transceiver 102, the processing unit 90 may store the digitized physiological signals 110 in the memory unit 98. In an alternative, the digitized signals 110 may not be transmitted and may instead simply be stored in the memory unit 98 for downloading at a later time.

In another alternative, the processing unit 90 may perform further processing on the digitized physiological signals 110 according to the type of physiological signal that is being recorded so that the transceiver 102 sends processed data that corresponds to the measured physiological signal rather than the actual measured physiological signals. The processed data may be readily displayed on the display 30 of the monitoring device 12. In another alternative, the processing unit 90 may perform further processing on the digitized physiological signal 110 according to the type of physiological signal that is being recorded so that the transceiver 102 sends averaged data collected over multiple stimulation sweeps.

The battery 100 of the wireless adapter 54 is a low voltage battery and the other components of the wireless adapter 54 are also adapted for low voltage operation. This reduces the possibility of electrical shock to the patient 16. In addition, this ensures that the battery 100 can operate for a long time before requiring replacement. In an alternative, the battery 100 may be rechargeable and the wireless adapter 54 may have an interface (not shown) to the battery 100 so that the battery 100 can be plugged into a battery charger and recharged.

Any suitable wireless communication protocol may be used for the monitoring device 12, the wireless sensor 14 and the wireless stimulator 32. In one embodiment, the Bluetooth standard is used as the wireless communication protocol. The Bluetooth standard provides a universal radio interface in the 2.4 GHz frequency band that enables low power electronic devices to wirelessly communicate with each other. In accordance with the Bluetooth standard, the monitoring device 12, the wireless sensors 14 and the wireless stimulator 32 behave as nodes grouped in an ad-hoc network referred to as a piconet. The monitoring device 12 behaves as a master node and the wireless sensors 14 and the wireless stimulator 32 behave as slave nodes. The monitoring device 12 and each of the wireless sensors 14 and the wireless stimulator 32 is provided with a unique address so that the wireless physiological signals 18 from various wireless sensors 14 can be distinguished from one another.

Each node in the Bluetooth network has an internal "native" clock that determines the timing of the corresponding transceiver. The communication channel between the master nodes and the slave nodes is defined by a frequency hopping sequence derived from the address of the master node. The master node provides its native clock as a time slot reference. Each time slot supports full-duplex communication initiated by the master node: during the first part of the time slot the master node polls a slave node and during the second part of the time slot the corresponding slave node responds.

During operation, the wireless sensors 14 are instructed by the monitoring device 12 to start and stop data transmission so that power and bandwidth is not wasted. Accordingly, the wireless sensors 14 are usually in a "listening mode" to wait for commands from the monitoring device 12. In particular, when the wireless adapter 54 is attached to one of the measurement modules 50 or 70, the wireless adapter 54 turns on, joins the piconet, identifies itself to monitoring device 12 and listens for commands. The wireless adapter 54 turns off when it is disconnected from the measurement module 50 or 70.

Some of the physiological monitoring and diagnostic tests performed by the physiological wireless monitoring system 10 require stringent timing requirements for the wireless sensors 14 and/or the wireless stimulator 32. One example is nerve conduction diagnostic tests and evoked potential monitoring in which synchronization is preferably done to within approximately +/−50 microseconds.

With the Bluetooth communication standard, the modulation rate of the master node is approximately 1 Mbit/sec which allows for synchronization down to 1 microsecond. This synchronization can be accomplished by adding extra hardware counting circuitry to the slave nodes, or by using the processors of the slave nodes, to keep track of the modulation rate of the master node. Each slave node will count at the same rate, but will have different zero points based on the time at which they started counting.

The method of aligning the respective zero points is to have the slave node transmit a timing message to the master node and have the master node immediately respond. The slave node then measures the number of counts of the master modulation rate taken for the round trip and divides by two to get the transit time. This is done many times, 50 times for example, to get an average transit time and the average clock offset (this is more accurate than individual measurements). The slave node then adjusts its native clock based on the average clock offset less the transit time to achieve the stated accuracy. This synchronization procedure is done each time a connection is established between a slave node and the master node.

An example of a diagnostic test that can be performed with the wireless physiological monitoring system 10 is the Palmar nerve response, in which the prongs 44 of the wireless stimulator 32 are placed in contact with the skin above the desired nerve to inject a stimulation current. One of the wireless sensors 14 is placed on a finger in close proximity to the desired nerve to measure the resulting action potential of the desired nerve. The Palmar nerve response usually occurs in about 1 millisecond. Measuring the latency of this response involves finding the take-off point or peak amplitude of the action potential. An error of 50 microseconds in synchronization results in a 5% error in the response, which is at the limit of what is diagnostically acceptable.

Some other examples of diagnostic tests and physiological monitoring that can be done with the wireless physiological monitoring system 10 include the blink reflex and recording somatosensory evoked potentials. These tests are demanding in that multiple action potentials are averaged together. This is done since the amplitude of the response is similar to the noise level in the measured signal, which is typically about 1 microvolt. Any errors in timing between stimulus delivery and data acquisition results in a flattened peak in the averaged response making it difficult to determine the latency of the response. If the synchronization errors exceed 50 microseconds then the quality of the responses is considered to be poor. Another example of physiological monitoring is the ECG which is typically recorded at a sampling rate of 200 Hz and requires 5 milliseconds of synchronization accuracy.

Bandwidth may be a factor in some of the monitoring/diagnostic tests that require multiple recording electrodes, such as multimodality monitoring during surgery in which somatosensory evoked potentials, motor evoked potentials, brainstem auditory evoked responses (BAERs), EMG and EEG are simultaneously recorded using up to 16 data channels that each acquire data at a sampling rate of 60 KHz or higher. Actually EEG and ECG signals require a sampling rate of 200 Hz, BAERs require a sampling rate of 60 kHz while most other evoked potentials require a sampling rate of 20 kHz. In addition, 16 bits are preferably used per sample. This results in a maximum possible data rate of approximately 15 Mbits/sec, which exceeds the capability of the Bluetooth standard, but is still within the range of 802.11g wireless communication standards.

Unfortunately, the power consumption of devices that operate under the 802.11g wireless standard is 3 times higher than devices that operate under the Bluetooth communication standard. This may be overcome by recording at a high speed triggered by the stimulus and storing the recorded and optionally processed physiological signals in the memory unit 98 of the wireless sensors 14 and then transmitting the recorded physiological signals from the wireless sensors 14 to the monitoring device 12 at lower speeds after the physiological response has occurred. This technique is applicable whenever continuous monitoring of the unprocessed waveform data is not required, such as for channels related to evoked potentials where only the averaged signals over multiple recording sweeps need be transmitted.

However, this technique does not work for channels related to EMG data which require continuous data transmission, but the EMG data can be sampled at lower frequencies.

It should further be noted that by storing and transmitting the data periodically, the transceiver 102 of the wireless adapter 54 can be turned off when not being used thereby saving power and extending the life of the battery 100. In addition, to save power consumption, data bandwidth can be reduced by employing at least one of decimation, averaging and compression. However, the power consumption due to the added processing must be smaller than the savings in power consumption due to transmitting a reduced amount of data.

The wireless physiological monitoring system of the invention is particularly well suited for wireless monitoring of ECG, EMG and EEG monitoring and can be used clinically, intra-operatively and in an Intensive Care Unit (ICU). In use, the wireless sensors 14 may be color-coded and/or numbered according to the corresponding placement location on the patient 16. Accordingly, a medical practitioner simply needs to refer only to the color-coding and/or numbering when attaching the wireless sensors 14 to the patient 16.

In order to conduct auditory or visual evoked potential testing, the wireless physiological monitoring system 10 may further include at least one of a wireless auditory stimulator and a wireless visual stimulator (both not shown). The wireless auditory stimulator may be a set of wireless headphones or at least one wireless insert earphone that may be used to present an auditory stimulus to the patient 16. The auditory stimulus may be a steady state waveform such as a tone, or a transient waveform such as a click, or some form of noise or a combination thereof in which the waveforms have a selectable phase, frequency and intensity. The wireless visual stimulator may be a set of goggles with a wireless link. The goggles may be used to provide steady state or transient visual stimuli such as a flash of light to at least one eye of the patient 16. In both the auditory and visual cases, the wireless sensors 14 are placed at the appropriate location on the patient 16 to record the resulting evoked potential.

It should be understood that various modifications can be made to the embodiments described and illustrated herein, without departing from the invention.

The invention claimed is:
1. A wireless physiological monitoring system for measuring physiological signals from a patient, comprising:
   a monitoring device, external to the patient, having a first transceiver;
   at least one wireless sensor disposed on a measurement site on the patient for measuring a physiological signal, the at least one wireless sensor having a second transceiver for transmitting a corresponding wireless physiological signal to the first transceiver;
   at least one wireless diagnostic stimulator having a third transceiver, the at least one wireless stimulator being adapted to provide a stimulation current to the patient in response to at least one of a command signal transmitted by the first transceiver of the monitoring device and manual actuation;
   wherein the at least one wireless sensor includes a wireless adapter comprising:
      the second transceiver;
      a measurement module having an active conductor and a reference conductor for receiving voltages used to produce a differential voltage measurement indicative of the physiological signal, the measurement module further including a common conductor for receiving another voltage for removing common mode voltage from the differential measurement; and a wireless needle assembly comprising the measurement module; and wherein the second transceiver transmits the differential measurement as the wireless physiological signal.

2. The system of claim 1, wherein the measurement module of the wireless needle assembly comprises:

a base having an electrical interface connected to the active, reference and common conductors, the base having a shape complementary to that of the wireless adapter for releasable attachment to the wireless adapter; and a shaft which houses the active, reference and common conductors, wherein a first conductor is disposed centrally along the longitudinal axis of the shaft, a second conductor is disposed concentrically about the first conductor, a first insulator is disposed in between the first and second conductors, a third conductor is disposed concentrically about the second conductor, and a second insulator is disposed in between the second and third conductors.

3. The system of claim 2, wherein the measurement module of the wireless needle assembly comprises:

a base having an electrical interface connected to the active, reference and common conductors, the base having a shape complementary to that of the wireless adapter for releasable attachment to the wireless adapter;

a needle shaft comprising the active and reference conductors; and a surface electrode comprising the common conductor.

4. The system of claim 3, wherein the measurement module of the wireless needle assembly comprises:

a base having an electrical interface connected to the active, reference and common conductors, the base having a shape complementary to that of the wireless adapter for releasable attachment to the wireless adapter;

a needle shaft comprising the active conductor; and surface electrodes comprising the reference and common conductors, respectively.

* * * * *